United States Patent [19]

Ibay et al.

[11] Patent Number: 5,206,341

[45] Date of Patent: Apr. 27, 1993

[54] POLYMERS FROM HYDROXY ACIDS AND POLYCARBOXYLIC ACIDS

[75] Inventors: Augusto C. Ibay; Linwood P. Tenney, both of Birmingham, Ala.

[73] Assignee: Southern Research Institute, Birmingham, Ala.

[21] Appl. No.: 795,776

[22] Filed: Nov. 21, 1991

[51] Int. Cl.⁵ .............................................. C08G 63/06
[52] U.S. Cl. .................................... 528/361; 528/271
[58] Field of Search ............................... 528/271, 361

[56] References Cited

U.S. PATENT DOCUMENTS

| | | |
|---|---|---|
| 2,363,103 | 11/1944 | Watson . |
| 2,433,721 | 12/1947 | Watson . |
| 2,449,828 | 9/1948 | Watson . |
| 2,453,559 | 11/1948 | Watson . |
| 2,555,385 | 6/1951 | Watson . |
| 3,284,417 | 11/1966 | Hostettler et al. . |
| 3,498,957 | 3/1970 | Jacobson . |
| 3,579,549 | 5/1971 | Stockmann . |
| 4,139,525 | 2/1979 | Baczkai . |
| 4,273,920 | 6/1981 | Nevin . |
| 4,507,445 | 3/1985 | Andrews ............................. 528/361 |

FOREIGN PATENT DOCUMENTS 584365 11/1959 Belgium .
4-13710 1/1992 Japan .

OTHER PUBLICATIONS

Fukuzaki, Hironobu et al, A New Biodegradable Pasty-type Copolymer of L-Lactic Acid and δ-Valerolactone With Relatively Low Molecular Weight for Application in Drug Delivery Systems. Journale of Controlled Release, 10 (1989) 293-303.

Fukuzaki, Hironubu et al, Synthesis of Copoly(D-,L-Lactic Acid) With Relatively Low Molecular Weight and In Vitro Degradation, Eur, Polym, J., vol. 25, No. 10, pp. 1019-1026, 1989.

Fukuzaki, Kironobu et al, Synthesis of low-molecular-weight copoly (L-lactic acid/ε-caprolactone) by direct copolycondensation in the absence of catalysts, and enzymatic degradation of the polymers. Polymer, 2990, vol. 31, Oct., pp. 2006-2014.

Fukuzaki, Hironobu et al, In vivo characteristics of low-molecular-weight copoly (-lactic acid/DL-hydroxyisocaproic acid) with parabolic-type and S-type degradation patterns, Makromol. Chem. 191, 731-736 (1990).

Fukuzaki, Hironobu et al, In vivo characteristics of low molecular weight copolymers composed of L-lactic acid and various DL-hydroxy acids as biodegradable carriers for drug delivery systems, Biomaterials 1990, vol. 11, Aug., pp. 441-446.

Fukuzaki, Hironobu et al, Direct Copolymerization of Glycolic Acid With Lactones In The Absence of Catalysts, Eur. Polym. J. vol. 26, No. 4, pp. 457-461, 1990.

Kazumichi, I. et al, Synthesis and in vitro degradations of low-molecular-weight copolyesters composted of L-lactic acid and aromatic hydroxy acids, Makromol. Chem. 191, 2077-2082 (1990).

Vancso-Szmercsanyi, I. et al, Metal-Containing Coordination Polymers. XIV.* Relations Between the Structure and the Melt Viscosity of Polyesters Containing MgIons, Journale of Polymer Science, Polymer Chemistry Edition, vol. 21, 1901-1911 (1983).

Connelly, R. W. et al, Melt Rheology of Ion-Containing Polymers. I. Effect of Ionic Content in a Model Polyesterionomer, Journal of Polymer Science: Polymer Physics Edition, vol. 20, 259-268 (1982).

Watson, Paul D., Lactic Acid Polymers As Constituents of Synthetic Resins and Coatings, Industrial and Engineering Chemistry, pp. 1393-1397, Aug. 1948.

Cottis, S. G. et al, Hydroxy Acids, Polymerization, Polymers, and Applications, pp. 311, 315, 316, 324, 348, 355-358.

Wanigatunga, S. et al, Siloxane-polypivololactone Thermoplastic Elastomers, Polymer Preprints, vol. 29, Nov. 2, pp. 320-321, Sep. 1988.

Blume, R. C, et al, Polypivalolactone Poly[1-Oxo-2,-2-Dimethyltrimethylene)], Macromolecular, Syntheses, vol. 7, pp. 39-42.

Rao, K. Balakoteswara et al, Ionomeric Interpretation of Thickening of Polyesters by Alkaline Earth Metal Oxides, Journal of Polymer Science: Polymer Chemistry Edition, vol. 23, 2135-2150 (1985).

English Translation of Japanese 4-13710.

68 Claims, No Drawings

PCT/US91/06299 to E. I. DuPont de Nemours and Company.

*Primary Examiner*—John Kight, III
*Assistant Examiner*—Shelley Weight
*Attorney, Agent, or Firm*—Pollock, Vande Sande & Priddy

[57] ABSTRACT

Copolymers from a hydroxy acid and a polycarboxylic component, method of preparation thereof, and use thereof are provided.

POLYMERS FROM HYDROXY ACIDS AND POLYCARBOXYLIC ACIDS

DESCRIPTION

1. Technical Field

The present invention is concerned with copolymers from a hydroxy carboxylic acid and a polycarboxylic acid and/or activated derivative thereof, and especially to such copolymers that are environmentally degradable and biosorbable. Moreover, the present invention is concerned with a process for preparing such polymers that results in achieving lower processing temperatures for the polymers along with providing mechanical properties that are comparable to biosorbable polyesters previously suggested. The reduced processing temperatures make it possible to melt blend heat-sensitive and solvent-sensitive materials with the polymers of the present invention.

2. Background Art

The demand for hydrolytically degradable and biosorbable synthetic polymers has significantly increased in recent years. For instance, use of such materials in a number of very diverse industries including paper, packaging, medical devices, for example sutures, and medical and agricultural delivery systems, has been proposed leading to the increased interest in hydrolytically degradable and bioresorbable polymers.

The suggested methods for preparing bioresorbable polyesters based on hydroxyalkanoic acids that possess suitable mechanical properties are ring-opening polymerization of lactones and fermentation. Those processes that involve ring-opening polymerization require the synthesis of cyclic monomers from hydroxyalkanoic acids or other suitable organic compounds. For instance, polyhydroxy acids, such as those polymers based on lactic acid and glycolic acid, in their more usable form, are prepared by ring-opening polymerization of their respective cyclic dimers, e.g. lactide and glycolide. Other bioresorbable polyesters have been prepared by ring-opening polymerization of such lactone monomers as δ-valerolactone and ε-caprolactone. Various poly(β-hydroxy acids) such as those with β-hydroxybutyrate repeating units, have been prepared by both ring-opening polymerization of B-butyrolactone and by fermentation.

However, such processes, as well as the polymers obtained therefrom, are not entirely satisfactory. For instance, certain of the polymers from hydroxy acids require three (3) separate synthetic processing steps for preparation. For example, in the preparation of polylactides or polyglycolides, the hydroxy alkanoic acid is first polycondensed to an oligomer and then pyrolysed into the corresponding lactide or glycolide monomer. The monomer is then purified by recrystallization and then polymerized. The pyrolysis step is quite energy intensive and requires temperatures of up to about 270° C.

These bioresorbable polymers exhibit relatively high melting points, which in turn require relatively high melt processing temperatures for the polymers. This is disadvantageous since many of the materials that are desirable additives to the polymers are heat sensitive such as various active pharmacological materials and active agricultural ingredients for delivery systems including controlled release formulations. Accordingly, for many formulations it has been necessary to employ solvent processing in order to combine such agents as pharmacological materials or proteins with the polymers. On the other hand, solvent processing is disadvantageous in that residual amounts of solvent invariably remain with the product since the solvents are difficult to remove completely from the final product.

SUMMARY OF THE INVENTION

The present invention overcomes the above-discussed problems associated with bioresorbable polymers. In particular, the hydrolytically degradable and biosorbable polymers of the present invention exhibit reduced processing temperatures, while at the same time achieving mechanical properties that are comparable to polymers prepared by processes discussed in the prior art. Typically, the polymers of the present invention can be melt processed at temperatures of about 50° C. to about 180° C. The term "biosorbable" as used herein refers to both bioresorbable and bioadsorbable polymers. A bioresorbable polymer is a polymer that breaks down in a living host into simple compounds that are known to be natural metabolites. The reaction causing breakdown can be the nonenzyme catalyzed action of water which can also occur in the environment. A bioadsorbable polymer is a polymer that breaks down in a living host by nonenzyme catalyzed direct action of water into simple compounds that are not natural metabolites but may or may not be metabolizable.

The polymers obtained by the present invention can be melt blended with heat-sensitive and solvent-sensitive material in view of the lower processing temperatures that can be employed with the polymers of the present invention. For example, the ability to employ lower processing temperatures permits melt blending of the polymer with pharmaceutical agents that may be heat-sensitive and/or solvent-sensitive. Moreover, the ability to employ lower processing temperatures makes it possible to provide delivery systems for pharmacological agents that have poor solubility and for various proteins that are easily denatured by solvents.

In particular, the present invention is concerned With a copolymer from a hydroxyalkanoic acid and a polycarboxylic component. The polycarboxylic component can be a single compound or polymer containing carboxylic acid functionality, and/or a reactive derivative thereof. Another aspect of the present invention is concerned with a copolymer from a hydroxyalkanoic acid, a polycarboxylic component as defined above, and a metallic compound.

Another aspect of the present invention is concerned with a process for producing the above copolymers. In particular, the process includes causing polycondensation of a hydroxyalkanoic acid in the presence of or while adding a polycarboxylic component of the type defined above prior to and/or during the polycondensation to thereby obtain a branched polymer in those instances where the carboxylic functionality are greater than two per molecule and a linear polymer where the carboxylic functionality are two.

A further aspect of the present invention includes a process for preparing the metal-containing polymers which includes causing polycondensation of a hydroxyalkanoic acid while adding a polycarboxylic component of the type defined above prior to and/or during the polycondensation to form a branched polymer; and then adding a metallic compound.

The above processes are capable of being carried out as one-pot processes as compared to multi-step synthesis required by the prior art.

Best and Various Modes for Carrying Out Invention

The hydroxy acids employed pursuant to the present invention contain only one primary or secondary reactive hydroxyl group and are preferably hydroxyalkanoic acids and most preferably monohydroxyalkanoic acids. If desired, the hydroxyacids can also contain tertiary hydroxyl groups, and/or aromatic hydroxyl groups (i.e. phenolic group). The hydroxy carboxylic acids are hydroxycarboxylic acids that are liquid at the reaction temperatures and typically contain from 2 to 22 carbon atoms and more typically 2 to 12 carbon atoms. If desired, the hydroxyacids can include heteroatoms such as nitrogen, oxygen, and sulfur. Examples of suitable hydroxyalkanoic acids are lactic acid; glycolic acid; $\beta$-hydroxybutyric acid; $\alpha$-hydroxybutyric acid; $\delta$-hydroxyvaleric acid; $\epsilon$-hydroxycaproic acid; $\alpha$-hydroxyisobutryic acid; $\alpha$-hydroxyvaleric acid; $\alpha$-hydroxycaproic acid; $\alpha$-hydroxy-$\alpha$-ethylbutyric; $\alpha$-hydroxyisocaproic acid; $\alpha$-hydroxy-$\alpha$-methylvaleric acid; $\alpha$-hydroxyheptanoic acid; $\alpha$-hydroxyoctanoic acid; $\alpha$-hydroxydecanoic acid; $\alpha$-hydroxymyristic acid; $\alpha$-hydroxystearic acid, and o-hydroxylignoceric acid. Examples of suitable hydroxy aromatic carboxylic acids include hydroxyalkyl substituted benzoic acids such as hydroxymethyl benzoic acid and 2-hydroxyethyl benzoic acid and mandelic acid (2-phenyl-2-hydroxy acetic acid). Examples of hydroxy acids containing heteroatoms include 2-hydroxyethoxy acetic acid, 3-hydroxypropoxy acetic acid, N-methyl-N-(2-hydroxyethyl) glycine and S-(2-hydroxyethyl) thioglycolic acid. Mixtures of such acids can be used, when desired. The preferred acids employed in the present invention are lactic acid glycolic acid acid, $\beta$-hydroxybutyric acid and $\alpha$-hydroxybutyric acid, $\beta$-hydroxypropanoic acid, $\alpha$-hydroxyvaleric acid, and $\alpha$-hydroxycaproic acid.

The polycarboxylic component employed pursuant to the present invention includes polycarboxylic acids, and/or activated derivatives thereof. The non-polymeric polycarboxylic acids preferably contain 2, 3 or 4 carboxylic acid groups. The polycarboxylic component employed is desirably free from primary and secondary hydroxyl groups. The polycarboxylic component can be saturated or ethylenically unsaturated and can include substituent groups such as nitrogen and amino groups. In addition, suitable carboxylic acids are the aliphatic carboxylic acids and aromatic carboxylic acids. Normally, the carboxylic acids contain 2 to 22 carbon atoms and preferably 4 to 13 carbon atoms. Examples of suitable polycarboxylic acids employed pursuant to the present invention are trimesic acid, succinic acid, fumaric acid, maleic acid, brassylic acid, adipic acid, ethylenediaminetetraacetic acid, nitrilotriacetic acid, citric acid, trimellitic acid, terephthalic acid, isophthalic acid, and pyromellitic acid.

The activated derivatives that can be employed are those derivatives of the polycarboxylic acids that are activated for producing esters and include ester derivatives, anhydrides, acyl halides, trialkylsilyl esters, acyl imidazoles, ketenes and O-acylureas. When the activated derivative includes a leaving group it is preferred that the by-product formed have a boiling point low enough to be volatilized from the reaction mixture. This is preferred since continuous removal of by-product shifts the equilibrium reaction towards product formation.

Suitable ester derivatives are methyl, ethyl, 1-propyl, 1-butyl, 1-pentyl, and 1-hexyl esters of the above carboxylic acids. Preferably the ester derivatives are alkyl esters having 1 to 6 carbon atoms.

The anhydride derivative when employed is a oyclic or linear polymeric anhydride of a dicarboxylic acid. A polymeric anhydride of a higher functionality monomeric carboxylic acid (e.g., tetra functional) would tend to result in a cross-linked polyanhydride that will not melt during the reaction with the hydroxy acid. When a cyclic or linear polymeric anhydride of a dicarboxylic acid is employed such typically has a molecular weight of less than about 10,000. Such polyanhydrides, as known in the art, can be prepared by a polycondensation of the dicarboxylic acid with acetic anhydride. Suitable anhydrides are phthalic anhydride, succinic anhydride, maleic anhydride, adipic anhydride, glutaric anhydride, polypyromellitic anhydride, polyterephthalic anhydride and polyisophthalic anhydride.

Suitable acyl halide derivatives include acyl bromides and acyl chlorides such as succinyl chloride, adipoyl chloride, terephthaloyl chloride, and isophthaloyl chloride. A suitable trialkylsilyl ester is trimethylsilyl ester. Suitable acyl imidazoles are succinyl imidazole and adipoyl imidazole. A suitable ketene derivative is obtained by dehydrohalogenation of acyl halide derivatives that contain an alpha-hydrogen and suitable O-acylureas are O-succinyl urea and O-adipoyl urea.

When the polycarboxylic component includes a monomeric ethylenically unsaturated acid or anhydride, such as fumaric acid, maleic acid or maleic anhydride, the reaction is such that the polycarboxylic component does not crosslink during the actual polycondensation, but rather has ethylenically unsaturated sites available for subsequent crosslinking after the polycondensation reaction. The subsequent crosslinking reaction can be a free-radical initiated process using, for example, a peroxide such as benzoyl peroxide or an azo-compound such as azobisisobutyronitrile. The crosslinking provides for enhanced mechanical properties.

In addition, the polycarboxylic component can be a polymer of a carboxylic acid or anhydride such as a polymer of an ethylenically unsaturated acid or anhydride. Suitable ethylenically unsaturated acids include ethylenically unsaturated monocarboxylic acids such as acrylic acid, methacrylic acid and crotonic acid. Suitable ethylenically unsaturated anhydrides include anhydrides of monoethylenically unsaturated dicarboxylic acids such as fumaric acid and maleic acid. In addition copolymers of such monomers with other monoethylenically and/or monoacetylenically unsaturated compounds such as ethylene, vinylacetate, vinylpyrrolidone and styrene can be employed. When employing a polymer, the polymer should be water soluble. Accordingly the number average molecular weight should be such that the polymer is water soluble and preferably is no more than about 40,000. In addition, when copolymers are used the amount of the acid and/or anhydride is typically at least about 10 mole % and more typically at least about 50 mole % of the monomers employed when the comonomer(s) forms a water soluble polymer (e.g.—vinylpyrrolidone) and typically at least about 50 mole % and more typically at least about 75 mole % of the monomers employed when the comonomer(s) would form a water insoluble polymer (e.g. —styrene and ethylene).

Mixtures of the polycarboxylic component can be used, when desired. For instance, mixtures are desirable to modify certain properties such as the degree of crystallinity by providing a mixture of branched and linear polymers as the product.

This can be accomplished with a mixture of a polycarboxylic component having a functionality of two with one having a functionality greater than two.

It is also contemplated pursuant to the present invention that the products of the present invention can be obtained by including auxiliary coreactants that do not cause crosslinking during condensation, and are present in amounts that do not cause the product to lose its biosorbability characteristic.

The polymers do not contain other di- and poly-functional reactants such as dihydroxyalkanes and polyols or monohydroxy alcohols in amounts that would result in the polymer having less than about 90% of its end groups being carboxyl end groups and are preferably free of such di- and poly-functional reactants and monohydroxy alcohols. It is important to the success of the present invention that at least about 90% of the end groups of the polymer and preferably about 100% of the end groups are carboxyl groups. This is especially important when the polymer is to be reacted with a metallic compound in order to achieve the desired salt linkage.

Examples of coreactants are amino acids such as glycine and thiol acids such as thioglycolic acid. When such coreactants are used, the amounts are typically up to about 50 mole % based upon the moles of hydroxy acid employed. For in vivo applications, in order that the polymers exhibit biosorbable properties, it is preferred that the hydroxycarboxylic acids as well as the polycarboxylic acids component be biosorbable. For non-medical applications, the polycarboxylic acid component need not be biosorbable.

The hydroxycarboxylic acid, pursuant to the present invention, is employed in an amount of about 99.95 mole percent to about 90 mole percent of the total moles of the hydroxy acid and reactive carboxylic moieties of the polycarboxylic component and preferably about 99 to about 99.9 mole percent. The reactive carboxylic moieties of the polycarboxylic component are correspondingly employed in amounts of about 0.05 to about 10 mole percent and preferably about 0.1 to about 1 mole percent of the total moles of hydroxy acid and reactive carboxylic moieties of the polycarboxylic component employed in the polymer.

The polymers generally have number average molecular weights of about 2,000 to about 10,000 and preferably number average molecular weight of about 3,000 to about 6,000. However, when the polycarboxylic component employed is a polymer of a carboxylic acid or anhydride thereof, the number average molecular weight of the polymer of the present invention can be increased by the molecular weight of the polymer which can be as much as about 10,000 to about 250,000 higher. The polymers may be linear or branched chain. When branched normally each branch is derived from a carboxylic acid moiety of the polycarboxylic component. The polymers preferably are in the form of having moieties from the hydroxy carboxylic acid being branched from a backbone of the moiety from the polycarboxylic component.

The polymers of the present invention typically are thermoplastic or thermoplastic elastomers. The polymers have physical properties such that they can be pulled into fibers.

Typically, the polymers of the present invention can be melt processed at temperatures of about 50° C. to about 180° C. Also, the polymers typically exhibit terminal flow at temperatures of about 110° C. to about 130° C. and more typically about 120° C. Terminal flow is that temperature at which the viscosity of the polymer no longer changes with an increase in temperature.

According to certain preferred aspects of the present invention the polymers are further prepared from a metallic compound such as an organometallic compound or metal salt that neutralizes carboxyl terminal groups present on the polymer. The use of the metallic compound is preferred but not absolutely necessary pursuant to the present invention. The metallic compounds when employed, are preferably employed in amounts sufficient to neutralize 0.1 to about 100% of the carboxyl terminal groups of the polymer preferably 10 to about 100% and most preferably about 20 to about 50% of the carboxyl terminal groups. The use of the metal results in obtaining ionic bonding between polymer chains rather than hydrogen bonding which results in somewhat better final properties for the polymer. The ionic bonds are more susceptible to exchange than are hydrogen bonds. Also, lower viscosities are obtained for the metal containing polymers as well as achieving polymers having enhanced toughness at room temperature. In addition, the polymers readily absorb water when in the salt form and break down relatively quickly.

The preferred metals are those that are physiologically acceptable so that the compositions can be used for medical purposes. In addition, the metals should have a valence of at least 2. Suitable metals include calcium, zinc, copper, iron, magnesium, cobalt and barium, and preferably calcium and zinc. The anion of the metal salts employed is preferably volatilizable from the reaction mixture. Suitable metal salts or organometallic compounds include zinc acetylacetonate, zinc acetate, zinc formate, zinc propionate, zinc bicarbonate and zinc carbonate as well as the corresponding calcium salts thereof. For non-medical uses, any other metal salts wherein the metal has a valence of at least two can be used.

The polymers of the present invention are prepared by the polycondensation of the hydroxyalkanoic acid. The polycarboxylic component can be added to the reaction at the start of the polycondensation or at any time during the polycondensation prior to completion of the polycondensation but normally not later than after 90% of the conversion has occurred as determined by viscosity measurements or amount of water collected. The preferred point of addition of the polycarboxylic acid is at the start of the reaction. The reaction is typically carried out at temperatures of about 160° C. to about 180° C. and require about 18 hours to about 24 hours, typical of which is about 24 hours.

The polymer formed is a virtual crosslinked or telechelic polymer with polycarboxylic functionalities at the branched terminals.

According to the most preferred aspects of the present invention, carboxyl terminal groups of the polymer are neutralized by adding a metallic compound to the reaction mixture typically after the polycondensation is substantially completed. The reaction with the metal salt is usually carried out for about 2 hours to about 18 hours, typical of which is about 2 hours.

If desired, the polymer can be purified by dissolving in a suitable solvent preferably those having relatively low boiling points of up to about 80° C. such as ethyl acetate, halogenated hydrocarbons, alcohols such as methanol, ethanol and isopropanol. The solution is then dried under vacuum. The polymer can then be processed into its desired form such as by milling into a powder.

In an alternative method, the reaction mass after the neutralization with the metallic compound is subjected to stripping of volatiles under vacuum of about 1 mm to about 3 mm Hg at about 100° to about 150° C., which helps in providing a more pure polymer. In particular, the presence of the metals under these conditions tend to catalyze the cyclization of any linear hydroxy acids that remain into the corresponding cyclic dimer, which readily separates from the desired polymers of the present invention.

The polymers of the present invention can be used for binders for sustained-release of various active ingredients such as drugs and agricultural materials such as fertilizers and herbicides. Also, the polymers can be used as binders or enteric coatings for drugs, as binders in cereals, as surgical devices such as surgical meshes and when in fiber form as sutures. In addition, those polymers that include the metal ions can be used for non-invasive monitoring of degradation of medical-implant applications because of its radiopacity.

The polymers of the present invention are readily processable and can be molded, machined or extruded depending upon the design requirements of the end product. For example, in the medical field the polymers may be used in the form of ligating clips, repair tacks, staples, pins, clamps, screws, plates, anastomotic devices, ocular inserts, disposable instruments, catheters, needles, vertebral discs, ostomy bags, temporary soft and hard tissue-augmentation devices, disposable contraceptive devices, fibers for sutures and for knitting or weaving into surgical mesh, burn dressings, stents, medicated dressings, dental packs, gauze, sponge, and absorbent swabs. In combination with other materials, the polymers of the present invention may be used as enteric coatings for pharmaceuticals; binder for drugs and peptides in microcapsules, pills, implants, intravaginals, and injectable controlled-release devices, fiber-reinforced composites for orthopedic applications; burn dressings in combination with drugs and other polymers; stents in combination with antithrombogenic agents; and coatings for medical devices.

For veterinary applications, the polymers of the present invention may be used in combination with pesticides and/or repellents for controlled-release flea-collars. Other controlled-release devices, similar to those used in medical application, have utility in veterinary applications for delivery of antibiotics, antivirals, and anti-inflammatories.

For agricultural applications, the polymers are applicable as seed coatings and agricultural mulch.

The polymers of the present invention are especially suitable as a controlled-release vehicle such as for fertilizers, plant-growth hormones, pesticide, herbicides, insect repellents and insect attractants.

Polymers of the present invention are suitable as binders in various processed foods such as cereals and candies.

For packaging applications, polymers of the present invention are suitable for molding containers such as bottles, as films for packaging, grocery bags, garbage and trash bags and as liquid foams. In addition, polymers of the present invention are suitable as hot-melt or contact adhesives, backing for disposable diapers, disposable signs, non-permanent inks, and coatings such as paints and polishes.

One specific application of the polymers of the present invention includes admixing the polymers with about 70% by weight of urea as an active ingredient to be employed as a sustained-release fertilizing composition.

The following non-limiting examples are presented to further illustrate the present invention:

EXAMPLE 1

Into a 1-L reaction kettle equipped with a mechanical stirrer, a thermometer to measure the pot temperature, a gas inlet adapter, and a distillation head are added about 600 grams of 88% DL-lactic acid and about 21.0 grams (0.1 mole) of trimesic acid (1,3,5-benzenetricarboxylic acid). With mechanical stirring and under a blanket of nitrogen, the reaction temperature is increased gradually up to about 140° C. to distill the water content and begin the polycondensation. In the first four hours, about 70 mL of water are distilled. The temperature is increased to about 160° C. and maintained for the next 18 hours to distill another 80 mL of water, at which point, no more water is distilled.

About 2.6 grams (0.01 mole) of zinc acetylacetonate is then added portion wise to the reaction mixture. Heating is continued for two hours under aspiration to remove any volatiles. The crude reaction mixture is cooled gradually. It is extrudable at 70 to 80° C. into fibers. However, fibers from the crude reaction mixture are somewhat brittle. The reaction mixture is dissolved in chloroform and precipitated with ethanol. A highly viscous liquid separated which is isolated and dried under vacuum to leave a crusty foam. The foam is crushed into powder. This powder melts at 70 to 80° C. and can be extruded into fibers with good mechanical properties. The polymer is moldable at about 50° C., is soluble in chloroform and insoluble in water and isopropyl alcohol.

EXAMPLE 2

Into a 2-L reaction kettle equipped with a mechanical stirrer, a thermometer to measure the pot temperature, a gas inlet adapter with a dip-tube above the level of reaction mixture, and a distillation head are added about 1.2 kilograms of 88% DL-lactic acid (11.7 mole) and about 28.86 grams (0.2 mole) of brassylic acid. With mechanical stirring and under a blanket of nitrogen, the reaction temperature is gradually increased up to about 180° C to distill the water content and begin the polycondensation. The 180° C. pot temperature is maintained for about 24 hours. At the end of 24 hours, the dip-tube of the gas inlet adapter is slid down and nitrogen is vigorously bubbled into the reaction mixture. The reaction mixture is purged for about 2 hours until no more volatiles can be collected. The distillate is collected and its volume compared to the theoretical amount of water from the reaction. The collection flask of the distillation is replaced and the dip-tube is slid up above the level of the reaction mixture with the nitrogen flow being maintained. The gas inlet adapter is temporarily disconnected and replaced with a powder addition funnel.

About 52 grams (0.2 mole) of zinc acetylacetonate are added to the reaction mixture via the powder addition funnel at a rate to keep the temperature of the reaction mixture from exceeding 180° C., and to control the evolution of gases. The acetylacetone condensed gases are collected and the volume can be noted. After the addition of zinc acetylacetonate is completed, the dip-tube is lowered back into the reaction mixture and purging is continued with nitrogen for about 2 hours until the evolution of volatiles has ceased. The heating is discontinued and the reaction mass is immediately poured into a Teflon sheet in a shallow baking pan. The polymer is permitted to cool to room temperature and then ground into fragments. The polymer fragments are cooled in liquid nitrogen and then ground using a Wiley mill. The polymer is solid at room temperature and is moldable at about 50° C. It is soluble in chloroform and insoluble in water and isopropyl alcohol.

EXAMPLE 3

Example 2 is repeated except that about 33.22 grams (0.2 mole) of terephthalic acid are used in place of the brassylic acid. The polymer has properties similar to those of Example 2.

EXAMPLE 4

Example 3 is repeated except that about 33.22 grams (0.2 mole) of isophthalic acid are used in place of the brassylic acid. The polymer has properties similar to those of Example 2.

EXAMPLE 5

Example 2 is repeated except that about 38.42 grams (0.2 mole) of citric acid are used in place of the brassylic acid. The polymer has properties similar to those of Example 2.

EXAMPLE 6

Example 2 is repeated except that about 28.10 grams (0.146 mole) of citric acid are used in place of the brassylic acid. The polymer has properties similar to those of Example 2.

EXAMPLE 7

Example 2 is repeated except that about 23.21 grams (0.2 mole) of fumaric acid are used in place of the brassylic acid. The polymer has properties similar to those of Example 2.

EXAMPLE 8

Example 2 is repeated except that about 29.22 grams (0.2 mole) of adipic acid are used in place of the brassylic acid. The polymer has properties similar to those of Example 2.

EXAMPLE 9

Example 2 is repeated except that about 23.61 grams (0.2 mole) of succinic acid are used in place of the brassylic acid. The polymer has properties similar to those of Example 2.

EXAMPLE 10

About 600 grams of 88% DL-lactic acid and about 30 grams of ethylenediamine tetraacetic acid are heated in a 3-neck flask equipped with a magnetic stirring bar, distillation head thermometer adapter and a gas inlet adapter. The pot temperature is raised to about 140° C. to distill of the water by-product. The reaction is continued for about 18 hours, after which the polymer is poured into a plastic container and cooled to room temperature. The polymer is fiber forming, except that in its crude form the fibers obtained are weaker than those obtained from purified polymer. Also, the unpurified polymer is somewhat brittle.

EXAMPLE 11

A) POLYCONDENSATION STEP

Into a 2-L reaction kettle, equipped with a mechanical stirrer, a thermometer to measure the pot temperature, a gas inlet adapter with a dip-tube above the level of reaction mixture, and a distillation head, are placed about 1.8 kilograms of 88% DL-lactic acid (17.55 mole) and about 5.65 grams (0.294 mole) of citric acid. With mechanical stirring in a nitrogen atmosphere, the reaction mass is gradually heated to about 180° C. to distill the water content and begin the polycondensation. The 180° C. pot temperature is maintained for about 24 hours. At the end of 24 hours, the gas-inlet adapter is replaced with a stopper (to shut off nitrogen flow), and the water-cooled condenser is replaced with an air-cooled distillation head. The distillation head is connected to a train of glassware that includes a distilling-trap adapter and a three-neck collection flask, which is chilled in a dry ice-isopropanol bath. A gas-inlet adapter with a connection for a manometer is attached to one of the side necks of the collection flask. To the other side neck is attached another gas-inlet adapter with a tubing connection to a Y-adapter. One of the remaining two openings of the Y-adapter is connected to a check valve. The other Y-adapter opening is connected to the vacuum trap in a Dewar container with dry ice-isopropanol, which is connected to the vacuum pump. Vacuum is applied (about 3 to about 10 mm Hg) until no more volatiles are collected. The pot-temperature is allowed to cool to 130° C. and the contents poured into five, wide-mouthed, shallow, plastic containers. The polymer is placed in the vacuum oven and vacuum (3 mm Hg) is applied overnight (18 hours) at 100° C. The polymer is allowed to cool to room temperature. The solid chunk of polymer is demolded and fractured into smaller fragments. A total of about 865.6 grams of the polymer is obtained and stored in a desiccator.

B) NEUTRALIZATION STEP

A 250-mL, three-neck, round bottom flask is fitted with a mechanical stirrer and a Claisen adapter with a thermometer and a gas-inlet adapter, (an outlet for gas flow). Into the flask is added about 100 grams of the polymer obtained above in the polycondensation step A) and about 1 gram of zinc acetylacetonate monohydrate. While under continuous flow of dry nitrogen, the mixture is heated to a pot temperature of 160° C. When the polymer becomes molten, stirring is started. The heating and stirring are continued for 18 hours. The fittings are removed from the reaction flask, and the open flask with its contents still molten is placed in a vacuum oven (about 3 mm Hg) at about 145° C. for at least about 18 hours. Without cooling, the contents of the flask are poured into a plastic container. The neutralized polymer is re-placed in a vacuum oven and allowed to cool to ambient temperature. The neutralized polymer is demolded from its container, broken into smaller fragments, and stored in a desiccator.

This example involved separating the polycondensation and neutralization steps into separate reaction vessels primarily as a convenience to be able to obtain from one polycondensation reaction, a number of examples of materials that vary only in their metal-ion content. Accordingly, it is apparent that the two separate steps can be carried out as a continuum in a single reaction pot, when desired.

EXAMPLE 12

The neutralization step of Example 11 is repeated with about 100 grams of the polymer obtained in the polycondensation step A) of Example 11 except that about 0.5 grams of zinc acetylacetonate monohydrate are employed.

EXAMPLE 13

The neutralization step of Example 11 is repeated with about 100 grams of the polymer obtained in the polycondensation step A) of Example 11 except that about 0.25 grams of zinc acetylacetonate monohydrate are employed.

What is claimed is:

1. A copolymer from a hydroxyalkanoic acid containing 2 to 22 carbon atoms and polycarboxylic component selected from the group consisting of non-polymeric polycarboxylic acid containing 2 to 22 carbon atoms, activated derivative thereof, water soluble homo-or copolymer of ethylenically unsaturated carboxylic acid, activated derivative thereof, and mixtures thereof, wherein the amount of said hydroxyalkanoic acid is about 99.95 mole % to about 90 mole % based upon the total moles of said hydroxyalkanoic acid and the reactive carboxylic moieties of the polycarboxylic component; and correspondingly said reactive carboxylic moieties of said polycarboxylic component is about 0.05 mole % to about 10 mole % based upon the total of said hydroxyalkanoic acid and said reactive moieties of polycarboxylic component. The end groups of said polymer are at least 90% carboxyl groups.

2. The copolymer of claim 1 wherein said hydroxycarboxylic acid consists essentially of an acid selected from the group consisting of lactic acid, glycolic acid; β-hydroxybutyric acid; α-hydroxybutyric acid; δ-hydroxyvaleric acid; ε-hydroxycaproic acid and mixtures thereof.

3. The copolymer of claim 1 wherein said polycarboxylic acid is non-polymeric and contains 2 to 22 carbon atoms.

4. The copolymer of claim 1 wherein said polycarboxylic component consists essentially of a polycarboxylic acid selected from the group consisting of trimesic acid, succinic acid, fumaric acid, maleic acid, brassylic acid, adipic acid, ethylenediaminetetraacetic acid, nitrilotriacetic acid, citric acid, trimellitic acid, terephthalic acid, isophthalic acid, pyromellitic acid, and mixtures thereof.

5. The copolymer of claim 1 wherein said amount of said hydroxycarboxylic acid is about 99 to about 99.9 mole % and correspondingly said amount of said reactive carboxylic moieties of the polycarboxylic component is about 1 to about 0.1 mole %.

6. The copolymer of claim 1 wherein said hydroxy carboxylic acid contains only one primary reactive hydroxy group or only one secondary reactive hydroxyl group.

7. The copolymer of claim 1 wherein said polycarboxylic component is selected from the group consisting of homo- or co-polymers of ethylenically unsaturated carboxylic acid or of an anhydride thereof, or of an ester thereof; and activated derivative of a non-polymeric polycarboxylic acid or of a polymeric polycarboxylic acid selected from the group consisting of esters, anhydrides, acyl halides, trialkylsilyl esters, acyl imidazoles, ketenes and 0-acylureas.

8. The copolymer of claim 1 wherein said activated derivative consists essentially of an alkyl ester having 1 to 6 carbon atoms.

9. The copolymer of claim 1 wherein said anhydride derivative is selected from the group consisting of polypyromellitic anhydride, polyterephthalic anhydride phthalic anhydride, succinic anhydride, maleic anhydride, adipic anhydride, glutaric anhydride, polyisophthalic anhydride, and mixtures thereof.

10. The copolymer of claim 1 wherein said hydroxycarboxylic acid consists essentially of lactic acid.

11. The copolymer of claim 1 wherein the average number molecular weight is about 2,000 to about 10,000.

12. The copolymer of claim 1 wherein the average number molecular weight is about 3,000 to about 6,000.

13. A copolymer from a hydroxycarboxylic acid and polycarboxylic component selected from the group consisting of polycarboxylic acid, activated derivative thereof, and mixtures thereof, wherein the amount of said hydroxycarboxylic acid is about 99.95 mole % to about 90 mole % based upon the total moles of said hydroxycarboxylic acid and the reactive carboxylic moieties of said polycarboxylic component; and correspondingly said reactive carboxylic moieties of said polycarboxylic component is about 0.05 mole % to about 10 mole % based upon the total of said hydroxycarboxylic acid and reactive carboxylic moieties of said polycarboxylic component, and a metallic compound.

14. The copolymer of claim 13 wherein the metal cation of said metallic compound has a valence of at least two.

15. The copolymer of claim 14 wherein said metallic compound consists essentially of a zinc or calcium salt or mixture thereof.

16. The copolymer of claim 13, wherein the average number molecular weight is about 2,000 to about 10,000.

17. A copolymer from a hydroxycarboxylic acid and polycarboxylic component selected from the group consisting of polycarboxylic acid, activated derivative thereof, and mixtures thereof, wherein the relative amount of said hydroxycarboxylic acid and polycarboxylic component is such that said copolymer has a maximum melting point of about 180° C., an average number molecular weight of about 2,000 to about 10,000, and at least about 90% of the terminal groups being carboxyl groups.

18. The copolymer of claim 17 wherein said hydroxycarboxylic acid is selected from the group consisting of lactic acid, glycolic acid, β-hydroxybutyric acid, α-hydroxybutyric acid, δ-hydroxyvaleric acid, ε-hydroxycaproic acid and mixtures thereof.

19. A copolymer from a hydroxycarboxylic acid and a polycarboxylic component selected from the group consisting of polycarboxylic acid, activated derivative thereof, and mixtures thereof, wherein the relative amount of said hydroxycarboxylic acid and polycarboxylic component is such that said copolymer has maximum melting point of about 180° C.; and a metallic compound.

20. The copolymer of claim 19 wherein the metal cation of said metallic compound has a valence of at least two.

21. The copolymer of claim 19 wherein said metallic compound consists essentially of a zinc or calcium salt or mixtures thereof.

22. A process for producing a copolymer which comprises:
   a) subjecting a hydroxycarboxylic acid to polycondensation,
   b) adding a polycarboxylic component prior to or during said polycondensation,
   c) causing said polycarboxylic component and hydroxycarboxylic acid to form a polymer; wherein said polycarboxylic component is selected from the group consisting of polycarboxylic acid, activated derivative thereof, and mixtures thereof, and wherein the relative amount of said hydroxycarboxylic acid and polycarboxylic component is such that said copolymer has a maximum melting point of about 180° C.

23. The process of claim 22 which further comprise reacting a metallic compound with said polymer.

24. The process of claim 23 wherein the metal cation of said metallic compound has a valence of at least two.

25. The copolymer obtained by the process of claim 22.

26. The copolymer obtained by the process of claim 23.

27. A fertilizer composition containing the copolymer of claim 1 and urea.

28. A fiber obtained from the copolymer of claim 1.

29. A fiber obtained from the copolymer of claim 13.

30. The fiber of claim 28 in the form of a suture.

31. The copolymer of claim 1 wherein said hydroxy carboxylic acid consists essentially of a hydroxyalkanoic acid containing 2 to 12 carbon atoms.

32. The copolymer of claim 1 wherein said activated derivative is selected from the group consisting of esters, anhydrides, acyl halides, trialkylsilyl esters, acyl imidazoles, ketenes and 0-acylureas.

33. The copolymer of claim 14 wherein said hydroxycarboxylic acid consists essentially of a hydroxyalkanoic acid containing 2 to 22 carbon atoms.

34. The copolymer of claim 13 wherein said hydroxy carboxylic acid consists essentially of a hydroxyalkanoic acid containing 2 to 12 carbon atoms.

35. The copolymer of claim 13 wherein the amount of said metallic compound is sufficient to neutralize about 0.1 to about 100% of the carboxylic terminal groups of the copolymer.

36. The copolymer of claim 13 wherein the metal cation of said metallic compound is selected from the group consisting of calcium, zinc, copper, iron, magnesium, cobalt, barium and mixtures thereof.

37. The copolymer of claim 13 wherein the anion of said metallic compound is selected from the groups consisting of acetylacetonate, acetate, formate, propionate, bicarbonate, carbonate and mixtures thereof.

38. The copolymer of claim 13 wherein said hydroxyalkanoic acid consists essentially of an acid selected from the group consisting of lactic acid, glycolic acid, β-hydroxybutyric acid, α-hydroxybutyric acid, δ-hydroxyvaleric acid, ε-hydroxycaproic acid and mixtures thereof.

39. The copolymer of claim 13 wherein said polycarboxylic acid contains 2 to 22 carbon atoms.

40. The copolymer of claim 13 wherein said polycarboxylic component consists essentially of a polycarboxylic acid selected from the group consisting of trimesic acid, succinic acid, fumaric acid, brassylic acid, adipic acid, ethylenediaminetetraacetic acid, nitrilotriacetic acid, citric acid, trimellitic acid, terephthalic acid, pyromellitic acid, and mixtures thereof.

41. The copolymer of claim 13 wherein said amount of said hydroxycarboxylic acid is about 99 to about 99.9 mole % and correspondingly said amount of said reactive carboxylic moieties of the polycarboxylic component is about 1 to about 0.1 mole %.

42. The copolymer of claim 13 wherein said hydroxy carboxylic acid contains only one primary reactive hydroxyl group or only one secondary reactive hydroxyl group.

43. The copolymer of claim 13 wherein said activated derivative is selected from the group consisting of esters, anhydrides, acyl halides, trialkylsilyl esters, acyl imidazoles, ketenes, and 0-acylureas.

44. The copolymer of claim 13 wherein said activated derivative consists essentially of an alkyl ester having 1 to 6 carbon atoms.

45. The copolymer of claim 13 wherein said anhydride derivative is selected from the group consisting of polypyromellitic anhydride, polyterephthalic anhydride phthalic anhydride, succinic anhydride, maleic anhydride, adipic anhydride, glutaric anhydride, polyisophthalic anhydride, and mixtures thereof.

46. The copolymer of claim 13 wherein said hydroxy carboxylic acid consists essentially of lactic acid.

47. The copolymer of claim 17 wherein said hydroxycarboxylic acid consists essentially of a hydroxyalkanoic acid containing 2 to 22 carbon atoms.

48. The copolymer of claim 47 wherein said polycarboxylic acid is selected from the group consisting of trimesic acid, succinic acid, fumaric acid, brassylic acid, adipic acid, ethylenediaminetetraacetic acid, nitrilotriacetic acid, citric acid, trimellitic acid, terephthalic acid, isophthalic acid, pyromellitic acid, and mixtures thereof.

49. The copolymer of claim 47 wherein said hydroxy alkanoic acid consists essentially of lactic acid.

50. The copolymer of claim 47 wherein said hydroxy carboxylic acid contains only one primary reactive hydroxy group or only one secondary reactive hydroxyl group.

51. The copolymer of claim 47 wherein said activated derivative is selected from the group consisting of esters, anhydrides, acyl halides, trialkylsilyl esters, acyl imidazoles, ketenes, and 0-acylureas.

52. The copolymer of claim 19 wherein the amount of said metallic compound is sufficient to neutralize about 0.1 to about 100% of the carboxyl terminal groups of the copolymer.

53. The copolymer of claim 19 wherein the anion of said metallic compound is selected from the group consisting of acetylacetonate, acetate, formate, propionate, bicarbonate, carbonate and mixtures thereof.

54. The copolymer of claim wherein said hydroxycarboxylic acid is selected from the group consisting of lactic acid, glycolic acid, β-hydroxybutyric acid, δ-hydroxybutyric acid, α-hydroxyvaleric acid, ε-hydroxycaproic acid and mixtures thereof.

55. The copolymer of claim 19 wherein said polycarboxylic acid is selected from the group consisting of trimesic acid, succinic acid, fumaric acid, brassylic acid, adipic acid, ethylenediaminetetraacetic acid, nitrilotriacetic acid, citric acid, trimellitic acid, terephthalic acid, isophthalic acid, pyromellitic acid, and mixtures thereof.

56. The copolymer of claim 19 wherein said hydroxy acid consists essentially of lactic acid.

57. The copolymer of claim wherein said hydroxy carboxylic acid contains only one primary reactive hydroxy group or only one secondary reactive hydroxyl group.

58. The copolymer of claim 19 wherein said activated derivative is selected from the group consisting of esters, anhydrides, acyl halides, trialkylsilyl esters, acyl imidazoles, ketenes and O-acylureas.

59. The process of claim 22 wherein the polycondensation is carried out at temperatures of about 160° to about 180° C.

60. The process of claim 22 wherein said hydroxycarboxylic acid consists essentially of hydroxyalkanoic acid containing 2 to 22 carbon atoms.

61. The process of claim 22 wherein said hydroxycarboxylic acid consists essentially of a hydroxyalkanoic acid containing 2 to 12 carbon atoms.

62. The process of claim 22 wherein the amount of said hydroxycarboxylic acid is about 99.95 mole % to about 90 mole % based upon the total moles of said hydroxycarboxylic acid and reactive carboxyl moieties of said polycarboxylic component; and corresponding said reactive carboxyl moieties of the polycarboxylic component is about 0.05 mole % to about 10 mole % based upon the total of said hydroxycarboxylic acid and reactive carboxyl moieties of the polycarboxylic component.

63. The process of claim 22 wherein said hydroxycarboxylic acid consists essentially of lactic acid.

64. The process of claim 22 wherein said polycarboxylic acid is selected from the group of trimesic acid, succinic acid, fumaric acid, brassylic acid, adipic acid, ethylenediaminetetraacetic acid, nitrilotriacetic acid, citric acid, trimellitic acid, terephthalic acid, isophthalic acid, pyromellitic acid and mixtures thereof.

65. The process of claim 23 wherein the amount of said metallic compound is sufficient to neutralize about 0.1 to about 100% of the carboxyl terminal groups of the copolymer.

66. The process of claim 23 wherein the metal cation of said metallic compound is selected from the group consisting of calcium, zinc, copper, iron, magnesium, cobalt, barium, and mixtures thereof.

67. The process of claim 23 wherein said metallic compound consists essentially of zinc or calcium salt or mixtures thereof.

68. The process of claim 23 wherein the anion of said metallic compound is selected from the group consisting of acetylacetonate, acetate, formate, propionate, bicarbonate, carbonate and mixtures thereof.

* * * * *